United States Patent [19]

Kirchhoff

[11] Patent Number: 4,826,997

[45] Date of Patent: May 2, 1989

[54] N-SUBSTITUTED ARYLCYCLO BUTENYL-MALEIMIDES

[75] Inventor: Robert A. Kirchhoff, Midland, Mich.

[73] Assignee: The Dow Chemical Company, Midland, Mich.

[21] Appl. No.: 893,125

[22] Filed: Aug. 4, 1986

Related U.S. Application Data

[63] Continuation-in-part of Ser. No. 644,849, Aug. 27, 1984, abandoned.

[51] Int. Cl.⁴ .............. C07D 207/452; C07D 207/456
[52] U.S. Cl. .................................... 548/546; 548/547; 548/548; 548/549; 546/281; 544/333
[58] Field of Search ............... 548/546, 547, 548, 549

[56]  References Cited

U.S. PATENT DOCUMENTS

| 3,053,851 | 9/1962 | Ladd | 548/549 |
|---|---|---|---|
| 3,658,843 | 4/1972 | Kleiner | 548/548 |
| 4,132,715 | 1/1979 | Roth | 548/522 |
| 4,540,763 | 9/1985 | Kirchhoff | 526/281 |
| 4,622,375 | 11/1986 | Wong | 526/284 |
| 4,638,078 | 1/1987 | Kirchhoff | 121/64 |
| 4,642,329 | 2/1987 | Kirchhoff et al. | 526/284 |
| 4,661,193 | 4/1987 | Kirchhoff et al. | 156/307.3 |
| 4,667,004 | 5/1987 | Wong | 526/284 |
| 4,667,005 | 5/1987 | Wong | 526/284 |
| 4,687,823 | 8/1987 | Kirchhoff et al. | 526/284 |
| 4,708,994 | 11/1987 | Wong | 525/392 |

FOREIGN PATENT DOCUMENTS 0193721  1/1986  European Pat. Off. .

Primary Examiner—David B. Springer
Attorney, Agent, or Firm—Norman L. Sims

[57]  ABSTRACT

The invention is a compound which comprises an unsaturated cyclic imide moiety and an aryl cyclobutene moiety, wherein the cyclobutene moiety is fused to the aryl radical, and wherein the imide nitrogen is connected to the aryl radical by a direct bond or a bridging member. Another aspect of this invention is a polyimide polymeric composition which results from the polymerization of the above-described compounds.

13 Claims, No Drawings

N-SUBSTITUTED ARYLCYCLO BUTENYL-MALEIMIDES

CROSS REFERENCE TO RELATED APPLICATIONS

This applications is a continuation-in-part of a co-pending application Ser. No. 644,849 filed Aug. 27, 1984, (incorporated herein by reference), abandoned.

BACKGROUND OF THE INVENTION

This invention relates to N-substituted arylcyclobuteno-unsaturated cyclic imides, and to novel polyimides prepared from such compounds.

In recent years the search for high performance materials, especially high temperature-resistant polymers, has gained momentum. In order for a material to have stability at high temperatures, it must fulfill several requirements including a high melting or softening temperature, a high modulus or rigidity, a resistance to solvent and chemical degradation, and toughness. The intrinsic thermal and oxidative stability of aromatic structures has long been recognized, and a variety of polymers have been made in which benzene rings are linked together by various connecting groups. Among the more stable aromatic polymers that fulfill the requirements of high temperature resistance are the polybenzimidazoles, the polyenzoxazoles and the polyimides. Of these polymers, the polyimides have had the most interest.

The major difficulty encountered in the commercial development of these materials is that they are usually obtained in the form of a powder which cannot be readily fabricated into useful objects.

The polyimides prepared from aliphatic diamines and aromatic carboxylic acids are generally soluble and thermoplastic. Aliphatic polyimides have been prepared from bis(dienophiles) and a diene such as cyclopentadiene. Such reactions often involve gas evolution.

Aromatic polyimides, such as polypyromellitimides, have a spectrum of superior properties. Those polyimides may be prepared by the reaction of an aromatic dianhydride with an aromatic diamine to give a soluble polyamic acid, which on cyclodehydration gives the insoluble desired product.

High performance plastics reduce the weight of mechanical components, and not just by virtue of their densities. Their high performance properties allow greater design stresses, and often elements can be downsized accordingly. In recent years, aromatic polyimides have become widely accepted as premium, high performance engineering plastics. These resins are well-known for having excellent properties at elevated temperatures (i.e., chemical resistance) but are also costly. Historically, polyimide resins are difficult to fabricate into objects other than fibers and films. The most common methods of manufacturing parts having the highest strength and temperature properties are hot compression-molding, machining from hot-compression molded or extruded rod, and direct forming (a process similar to the powder-metallurgy processes). Given the synthetic and fabrication difficulties, a new route to polyimides is desirable.

A further problem with the preparation of certain polyimides is the need for the use of catalysts, initiators or curing agents. The presence of such compounds often results in the preparation of impure polymeric compositions. Further, the presence of such compounds often results in undesirable properties in such polymeric compositions. What are needed are monomers which are prepare polyimides wherein the polymers can be easily processed, for example, fabricated into useful objects. What are further needed are monomers which can be polymerizable in a manner such that no gas is evolved. What are further needed are monomers which can be polymerized without the need for catalysts curing agents or initiators.

SUMMARY OF THE INVENTION

The invention is a compound which comprises an unsaturated cyclic imide moiety and an aryl cyclobutene moiety, wherein the cyclobutene moiety is fused to the aryl radical, and wherein the imide nitrogen is connected to the aryl radical by a bridging member or a direct bond.

Another aspect of this invention is a polyimide polymeric composition which results from the polymerization of one or more of the above-described compounds.

The novel compounds of this invention are easily processable into useful articles. The polymerization of such compounds does not result in the evolution of gaseous or volatile by-products which can create problems in the eventual product prepared. Furthermore, in order to prepare the polymers of these monomers, there is no need for catalysts, initiators or curing agents.

DETAILED DESCRIPTION OF THE INVENTION

In general, the compounds of this invention comprise unsaturated cyclic imides which are N-substituted with arylcyclobutene moieties. In such arylcyclobutene moieties the cyclobutene ring is fused to the aromatic radical. The nitrogen atom of the cyclic imide is connected to the aryl radical of the arylcyclobutene moiety by a bridging member or a direct bond. The cyclic imide can be substituted with hydrocarbyl, hydrocarbyloxy or hydrocarblythio substituents. The aryl radical on the arylcyclobutene moiety can be substituted with electron-withdrawing groups, electron-donating groups, hydrocarbyl groups, hydrocarbyloxy groups or hydrocarbylthio groups. The cyclobutene ring may be substituted with electron-withdrawing groups or electron donating groups.

The cyclic imide can be any cyclic imide moiety which contains olefinic unsaturation, and which may be substituted in the manner described hereinbefore. It is preferable that the olefinic unsaturation be adjacent to one of the carbonyl moieties of the imide functionality. In one preferred embodiment, the cyclic imide is a 5-membered heterocycle, in particular, a maleimide. Preferably, the substituents which may be on the carbon atoms of the imide ring are $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ alkaryl, $C_{7-20}$ aralkoxy or $C_{7-20}$ aralkylthio. More preferred substituents include $C_{1-20}$ alkyl, with $C_{1-3}$ alkyl being most preferred.

The arylcyclobutene moiety can be any aromatic radical which has a cyclobutene ring fused to one of the aromatic rings. The term "aryl" refers herein to any aromatic radical. Aromatic as used herein refers to carbocyclic or heterocyclic rings in which $4n+2$ delocalized $\pi$ electrons are contained in an orbital ring. This property is also known as resonance stabilization or delocalization. Preferred carbocyclic aromatic radicals include benzene, naphthalene, phenanthrene, anthracene, a biaryl radical, or two or more aromatic radicals bridged by alkylene or cycloalkylene moieties. More preferred carbocyclic aromatic radicals include benzene, naphthalene, biphenyl, binaphthyl or a diphenylalkylene or a diphenylcycloalkylene compound. The most preferred carbocyclic aromatic radical is benzene. Examples of preferred heterocyclic aromatic compounds included pyrrole, furan, thiophene, imidazole, oxazole, thiazole, pyrazole, pyridin, and pyrimidine. More preferred heterocyclic aromatic compounds are pyridine, furan, and thiophene, with pyridine being most preferred. The carbocyclic aromatic rings are preferred over the heterocyclic aromatic rings.

The aryl radical can be subsituted with electron-withdrawing groups, electron-donating groups, hydrocarbyloxy groups, hydrocarbyl groups or hydrocarbylthio groups. Electron-withdrawing groups refer herein to cyano, carboxylate, hydrocarbylcarbonyloxy, nitro, halo, hydrocarbylsulfinyl or hydrocarbylsulfonyl groups. Electron-donating groups refer herein to amino groups, hydroxy groups or alkyl groups. Preferred substituents on the aryl radical include $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy, $C_{7-20}$ aralkylthio, cyano, carboxylate, hydrocarbylcarbonyloxy, nitro, halo, hydrocarbylsulfinyl, amino or hydrocarbylsulfonyl. More preferred substituents on the aryl radical include $C_{1-20}$ alkyl, halo, nitro or cyano. The most preferred substituents on the aryl moiety include $C_{1-3}$ alkyl, halo, nitro or cyano.

The cyclobutene ring may be substituted with electron-withdrawing groups or electron donating groups, wherein electron withdrawing groups and electron-donating groups are described hereinbefore. Preferred substituents on the cyclobutene ring are cyano, carboxylate, hydrocarbylcarbonyloxy, nitro, halo, hydrocarbylsulfonyl or hydrocarbylsulfinyl. More preferred substituents include halo, nitro or cyano groups; with cyano groups being most preferred.

The bridging member can be a divalent organic radical which is bonded to the nitrogen of the cyclic imide and the aryl radical of the arylcyclobutene moiety. The divalent organic radical useful as a bridging member is any divalent organic radical which is capable of being bonded to both the nitrogen of a cyclic imide and an aryl radical. The divalent organic radical is preferably a hydrocarbylene, hydrocarbyleneamido, hydrocarbylenecarbonyloxy, hydrocarbyleneoxy, hydrocarbylenethio, hydrocarbylenesulfinyl or hydrocarbylenesulfonyl radical. More preferred divalent organic radicals are alkylene, arylene, alkylene-bridged polyarylene, cycloalkylene-bridged polyarylene, alkyleneamido, aryleneamido, alkylene-bridged polyaryleneamido, cycloalkylene-bridged polyaryleneamido, alkylenecarbonyloxy, arylenecarbonyloxy, alkylene-bridged polyarylenecarbonyloxy, cycloalkylene-bridged polyarylenecarbonyloxy, alkyleneoxy, aryleneoxy, alkylene-bridged polyaryleneoxy, cycloalkylene-bridged polyaryleneoxy, alkylenethio, arylenethio, alkylene-bridged polyarylenethio, cycloalkylene-bridged polyarylenethio, alkylenesulfinyl, arylenesulfinyl, alkylenebridged polyarylenesulfinyl, cycloalkylene-bridged polyarylenesulfinyl, alkylenesulfonyl, arylenesulfonyl, alkylene-bridged polyarylenesulfonyl or cycloalkylene-bridged polyarylenesulfonyl. Even more preferred divalent organic radicals include alkylene, arylene, alkylenecarbonyloxy, arylenecarbonyloxy, alkyleneamido, aryleneamido, alkyleneoxy, aryleneoxy, alkylenethio or arylenethio. Most preferred divalent organic radicals include alkylene and arylene radicals.

Preferably, the aryl moiety and cyclic imide are connected by a direct bond or a bridging member which comprises an alkylene, arylene, alkylene-bridged polyarylene or cycloalkylene-bridged polyarylene; and more preferably a direct bond or a bridged polyarylene; and more preferably a direct bond or a bridging member which comprises an alkylene or arylene moiety. Most preferably the cyclic imide nitrogen and the aryl radical are connected by a direct bond.

Preferred N-substituted arylcyclobutenyl cyclic imides correspond to the formula

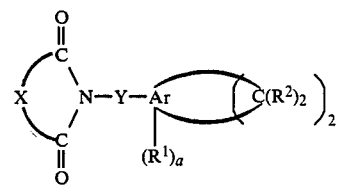

wherein

Ar is an aromatic radical;

$R^1$ is separately in each occurrence a hydrocarbyl, hydrocarbyloxy, hydrocarbylthio, electron-donating or electron-withdrawing group;

$R^2$ is separately in each occurrence hydrogen or an electron-withdrawing group;

X is an alkenylene moiety which can be substituted with one or more hydrocarbyl, hydrocarbyloxy or hydrocarbylthio groups;

Y is a direct bond or divalent organic moiety; and a is an integer of between about 0 and 3.

More preferred N-substituted arylcyclobutenyl-unsaturated cyclic imides include those which correspond to the formula

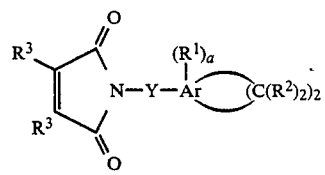

wherein

Ar is an aromatic radical;

$R^1$ is separately in each occurrence a hydrocarbyl, hydrocarbyloxy, hydrocarbylthio, an electron-donating or elctron-withdrawing group;

$R^2$ is separately in each occurrence hydrogen or an electron-withdrawing group;

$R^3$ is separately in each occurrence hydrogen, a hydrocarbyl, hydrocarbyloxy or hydrocarbylthio group;

Y is a direct bond or a divalent organic radical; and a is an integer of between about 0 and 3.

In an even more preferred embodiment, the N-substituted arylcyclobutenyl-unsaturated cyclic imide corresponds to the formula

[Structure shown at top left: a maleimide-type ring with two R³ groups and two C=O groups, connected via N—Y to a benzene ring bearing (R¹)_b substituents and fused to a cyclobutane ring bearing two (R²)₂ groups.]

wherein
$R^1$ is separately in each occurrence a hydrocarbyl, hydrocarbylthio, hydrocarbyloxy, electron-withdrawing or electron-donating group;
$R^2$ is separately in each occurrrence hydrogen or an electron-withdrawing group;
$R^3$ is separately in each occurrence hydrogen, hydrocarbyl, hydrocarbyloxy or hydrocarbylthio;
Y is a direct bond or a divalent organic radical; and
b is an integer of between 0 and 3, inclusive.

In the above formulas, $R^1$ is preferably $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ aralkoxy, $C_{7-20}$ alkaryloxy, $C_{7-20}$ alkarylthio, $C_{7-20}$ aralky, $C_{7-20}$ aralkoxy, $C_{7-20}$ aralkylthio, cyano, carboxylate, hydrocarbylcarbonyloxy, nitro, halo, hydrocarbylsulfinyl, hydrocarbylsulfonyl or amino. $R^1$ is more preferably $C_{1-20}$ alkyl, halo, nitro or cyano. Most preferably $R^1$ is $C_{1-3}$ alkyl, halo, nitro or cyano.

$R^2$ is preferably hydrogen, cyano, carboxylate, hydrocarbylcarbonyloxy, nitro, halo, hydrocarbylsulfonyl hydrocarbylsulfinyl, alkyl, amido, hydrocarbyloxy. $R^2$ is more preferably hydrogen, halo, nitro or cyano. $R^2$ is even more preferably hydrogen or cyano and most preferably hydrogen.

$R^3$ is preferably hydrogen, $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy or $C_{7-20}$ aralkylthio. $R^3$ is more preferably hydrogen or $C_{1-20}$ alkyl. $R^3$ is even more preferably hydrogen or $C_{1-3}$ alkyl and most preferably hydrogen.

In the above formulas, Y is preferably a direct bond, a hydrocarbylene, hydrocarbyleneamido, hydrocarbylenecarbonyloxy, hydrocarbyleneoxy, hydrocarbyleneaminio, hydrocarbylenecarbonyl, hydrocarbylenethio, hydrocarbylenepolythio, hydrocarbylenesulfinyl or hydrocarbylenesulfonyl. Y is more preferably a direct bond, alkylene, arylene, alkylene-bridged polyarylene, cycloalkylene-bridged polyarylene, alkyleneamido, aryleneamido, alkylenecarbonyloxy, arylenecarbonyloxy, arylenecarbonyl, alkylenecarbonyl, aryleneoxy, alkyleneoxy, aryleneoxy, aryleneamino, alkyleneamino, alkylenethio, alkylenepolythio, arylenethio, arylenepolythio, arylenesulfinyl, alkylenesulfinyl, arylenesulfonyl or alkylenesulfonyl. Y is most preferably a direct bond, alkylene or arylene.

In the formulas described hereinbefore, Ar is preferably a benzene, naphthalene, phenanthrene, anthracene or biaryl radical, or two or more aromatic radicals bridged by alkylene moieties. Ar is more preferably benzene, naphthalene, biphenyl, binaphthyl or diphenylalkylene. Ar is more preferably a benzene radical.

Hydrocarbyl means herein an organic radical containing carbon and hydrogen atoms. The term hydrocarbyl includes the following organic radicals: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is, cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups. $C_{1-5}$ alkyl includes methyl, ethyl, propyl, butyl and pentyl.

Cycloalkyl refers to alkyl groups containing one, two, three or more cyclic rings. Cycloalkenyl refers to mono, di- and polycyclic groups containing one or more double bonds. Cycloalkenyl also refers to cycloalkenyl grups wherein two or more double bonds are present.

Hydrocarbylene herein refers to a divalent hydrocarbon radical and is analogous to the hydrocarbyl radicals described hereinbefore with the single difference that the hydrocarbylene radical is divalent.

Hydrocarbyleneamido refers herein to a divalent radical wherein a hydrocarbylene radical is bonded to an amido group, and corresponds to the formula $$-R^4-\overset{\overset{O}{\|}}{C}\overset{}{\underset{R^5}{N}}-$$

wherein $R^4$ is a hydrocarbylene radical and $R^5$ is hydrogen or a hydrocarbyl radical.

Hydrocarbyleneoxy refers herein to a divalent radical in which a hydrocarbylene radical is bonded to divalent oxygen atom and corresponds to the formula $-R^4-O-$ wherein $R^4$ is as defined hereinbefore.

Hydrocarbylenecaronbyloxy refers to a hydrocarbylene moiety which is bonded to a carbonyl moiety which is further bonded to a divalent oxygen atom and corresponds to the formula $$-R^4-\overset{\overset{O}{\|}}{C}O-$$

wherein $R^4$ is as defined hereinbefore.

Hydrocarbylenethio refers herein to a radical in which a hydrocarbylene radical is further bonded to one or more sulfur moieties and corresponds to the formula $-R^4-(S)_p-$ wherein $R^4$ is as hereinbefore defined, and wherein p is between 1 and 3.

Hydrocarbyleneamino refers to a hydrocarbylene radical bonded to an amino moiety and generally corresponds to the formula $$-R^4-\underset{R^5}{N}-$$

wherein $R^4$ and $R^5$ are as defined hereinbefore.

Hydrocarbylenesulfinyl refers herein to a hydrocarbylene moiety bonded to a sulfinyl moiety and generally corresponds to the formula

wherein $R^4$ is as hereinbefore defined.

Hydrocarbylenesulfonyl generally corresponds to a radical in which a hydrocarbylene radical is bonded to a sulfonyl radical and corresponds to the formula

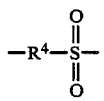

wherein $R^4$ is as hereinbefore defined.

Wherein the bridging member is a hydrocarbyleneamido, hydrocarbyleneoxy, hydrocarbyleneamino, hydrocarbylenethio, hydrocarbylenecarbonyloxy moiety, the amido, amino, oxy, thio, sulfinyl or sulfonyl moiety is preferably bonded to the aryl portion of the arylcyclobutene.

Examples of preferred N-substituted benzocyclobutenyl maleimides include N-benzocyclobutenyl maleimide, N-benzocyclobutenylmethyl maleimide, N-benzocyclobutenylethyl maleimide, N-benzocyclobutenylpropyl maleimide, N-benzocyclobutenylbutyl maleimide, N-benzocyclobutenylpentyl maleimide, N-benzocyclobutenylhexyl maleimide, N-benzocyclobutenylphenyl maleimide, N-benzocyclobutenylbiphenyl maleimide, N-benzocyclobutenylamidomethyl maleimide, N-benzocyclobutenylamidoethyl maleimide, N-benzocyclobutenylamidopropyl maleimide, N-benzocyclobutenylamidobutyl maleimide, N-benzocyclobutenylamidopentyl maleimide, N-benzocyclobutenylamidohexyl maleimide, N-benzocyclobutenylamidobiphenyl maleimide, N-benzocyclobutenyloxycarbonylmethyl maleimide, N-benzocyclobutenyloxycarbonylethyl maleimide, N-benzocyclobutenyloxycarbonylpropyl maleimide, N-benzocyclobutenyloxycarbonylbutyl maleimide, N-benzocyclobutenyloxycarbonylpentyl maleimide, N-benzocyclobutenyloxycarbonylhexyl maleimide, N-benzocyclobutenyloxycarbonylphenyl maleimide, N-benzocyclobutenyloxycarbonylbiphenyl maleimide, N-benzocyclobutenylthiomethyl maleimide, N-benzocyclobutenylthioethyl maleimide, N-benzocyclobutenylthiopropyl maleimide, N-benzocyclobutenylthiobutyl maleimide, N-benzocyclobutenylthiopentyl maleimide, N-benzocyclobutenylthiohexyl maleimide, N-benzocyclobutenylthiophenyl maleimide, N-benzocyclobutenylthiobiphenyl maleimide, N-benzocyclobutenyloxymethyl maleimide, N-benzocyclobutenyloxyethyl maleimide, N-benzocyclobutenyloxypropyl maleimide, N-benzocyclobutenyloxybutyl maleimide, N-benzocyclobutenyloxypentyl maleimide, N-benzocyclobutenyloxyhexyl maleimide, N-benzocyclobutenyloxyphenyl maleimide, N-benzocyclobutenyloxybiphenyl maleimide.

The arylcyclobutene moieties can be prepared by several synthesis schemes.

In one synthesis scheme, an alkyl-substituted aromatic compound which is further substituted with an aryl deactivating substituent is chloroalkylated in a position ortho to the alkyl group. In the preferred embodiment wherein the aromatic compound is benzene, the starting material corresponds to the following formula

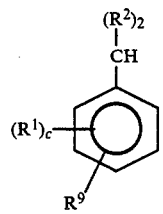

wherein $R^1$ and $R^2$ are defined hereinbefore; $R^9$ is any aryl deactivating substituent; and c is an integer of 0, 1, 2, or 3. The alkyl N-substituted aromatic compound is chloroalkylated by contacting the alkyl aromatic compound with a chloroalkylating agent and thionyl chloride in the presence of an iron chloride catalyst so as to result in a product which contains a chloroalkyl group ortho to the alkyl substituent. In the embodiment wherein the aromatic compound is a benzene ring, the product corresponds to the formula

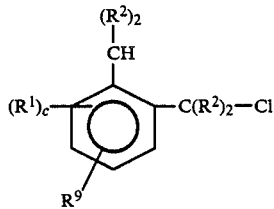

wherein $R^9$ is a hydrocarbyloxycarbonyl, carboxamide, hydrocarbylcarbonyl, carboxylate, halocarbonyl, nitrile, nitro, sulfone or sulfoxide group. $R^9$ is more preferably a halo or hydrocarbyloxycarbonyl group, with hydrocarbyloxycarbonyl being the most preferred group. Preferably c is 0 to 1, most preferably 0.

In this process the chloroalkylating agent is preferably chloromethyl methyl ether, although other chloroalkylating agents such as bis(chloromethyl) ether could be used. At least a 2:1 molar excess of the chloroalkylating agent to the alkyl-substituted aromatic compound is needed. It is preferable to use between about a 6:1 and 3:1 ratio of chloroalkylating agent to alkyl aromatic compound. The catalyst is ferric chloride ($FeCl_3$) while the cocatalyst is thionyl chloride. The catalyst can be present in between about 0.1 and 1.0 mole per mole of alkyl aromatic. More preferably between about 0.2 and 0.4 mole of catalyst are present for each mole of alkyl aromatic compound. Preferably between about 0.1 and 1.0 mole of thionyl chloride per mole of alkyl aromatic is used, more preferably between about 0.2 and 0.4 mole per mole of alkyl aromatic.

This process can be performed at a temperature of between about 40° C. and 80° C., preferably about 40° C. and 60° C. Below about 40° C., the reaction rate is low. The boiling point of some of the components of the reaction mixture starts at about 80° C.

This process can be done by contacting the alkyl aromatic compound with the chloromethylating agent, catalyst and cocatalyst in a suitable solvent. Suitable solvents include chlorinated hydrocarbon solvents. Thereafter the reaction mixture is heated to the appropriate temperature.

The product can be recovered by quenching the reaction mixture with alcohols or water to inactivate the chloroalkylating agents remaining, stripping off the volatiles and washing out the catalyst with water. The product thereafter is recovered by distillation.

The ortho chloroalkylated alkyl aromatic compounds can be converted to aromatic compounds with cyclobutene rings fused thereto, by pyrolysis. This is achieved by contacting the ortho chloroalkylated alkyl aromatic compound with at least 2 times its weight of a suitable diluent, and thereafter passing the mixture through a reactor at a temperature of 550° C. or greater and a pressure of between about atmospheric and 25 mm of mercury. Suitable diluents are generally substituted aromatic compounds which are inert to the chloromethylated alkyl aromatic compound and are stable at pyrolysis temperatures. Examples of suitable diluents are benzene, toluene, xylenes, chlorobenzenes, nitrobenzenes, methylbenzoates, phenyl acetate or diphenyl acetate. Preferred diluents are the xylenes. Preferable temperatures are between about 700° C. and 750° C. Preferable pressures are between about 35 and 25 mm of mercury. In a preferred embodiment, the reaction mixture is passed through a hot tube packed with an inert material, for example, quartz chips or stainless steel helices. The product can be recovered by distillation. The product wherein the aromatic compound is benzene corresponds to the formula

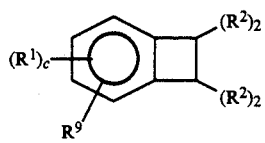

wherein $R^1$, $R^2$, $R^9$ and c are as hereinbefore defined.

In the preferred embodiment wherein $R^9$ is a hydrocarbyloxy carbonyl moiety, the hydrocarbyloxy carbonyl moiety can be converted to a carboxylate moiety by contacting the substituted (arylcyclobutene) compound with at least a molar equivalent of alkali metal hydroxide in an alkanol-water solvent system. In the embodiment wherein the aromatic radical is benzene, the product corresponds to the formula

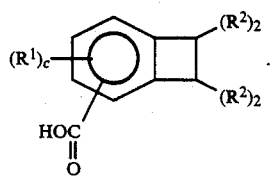

Thereafter the carboxylate-substituted (arylcyclobutene) compound can be converted to an acid chloride by contacting the carboxylate-substituted (arcycyclobutene) compound with thionyl chloride and refluxing at 70° C. to 80° C. The acid halide-substituted (arylcyclobutene) so formed can be used to prepare the novel monomers of this invention, as described hereinafter. In the embodiment wherein the aryl radical is a benzene ring, the product corresponds to the formula

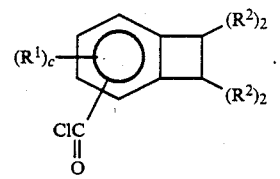

In an alternative synthesis, an aryl compound with ortho dibromomethyl groups can be converted to a 1,2-diiodoarylcyclobutene, by contacting the aryl compound substituted with ortho dibromomethyl moieties with an alkali metal iodide in an alkanol solvent at reflux so as to form the diiodoarylcyclobutenes. The product can be recovered by filtering, evaporating the filtrate and recrystallizing the product. In the embodiment wherein the aryl radical is a benzene radical, the starting material corresponds to the formula

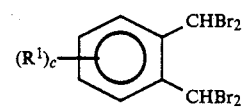

and the iodobenzocyclobutene corresponds to the formula

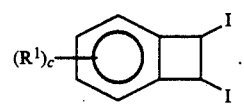

The 1,2-diiodoarylcyclobutenes can be converted to arylcyclobutenes by dissolving the 1,2-diiodoarylcyclobutenes in an alochol solvent, preferably methanol or ethanol and contacting the solution with an alkali metal hydroxide in the presence of a palladium-on-carbon catalyst and $H_2$ gas at a temperature of 20° C. to 30° C. In general, at least between about 2 and 4 moles of alkali metal hydroxide per mole of 1,2-diiodoarylcyclobutene is used. Preferably, between about 50 and 200 psi of hydrogen gas is used. The arylcyclobutenes prepared in this manner can be recovered by distillation. In the embodiment wherein the aryl radical is a benzene radical, the product corresponds to the formula

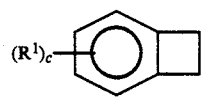

The arylcyclobutene is thereafter brominated. In this process, the arylcyclobutene is dissolved in acetic acid and contacted with a brominating agent of pyridinium hydrobromide perbromide in the presence of mercuric salts, for example, mercuric acetate, at a temperature of between about 20° C. and 50° C. The brominated product can be recovered by extraction and distillation. In the embodiment wherein aryl radical is benzene, the product corresponds to the formula

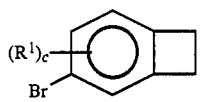

The brominated arylcyclobutene can thereafter be carbonylated to prepare a hydrocarbyloxy carbonyl-substituted arylcyclobutene. This carbonylation is achieved by dissolving the brominated arylcyclobutene in an alkanol solvent, and thereafter contacting the solution with carbon monoxide under pressure in the presence of a palladium catalyst, wherein the palladium is in the zero valence state, in the further presence of an acid acceptor under conditions such that the brominated arylcyclobutene compound undergoes carbonylation. Preferred catalysts are palladium acetate with a cocatalyst of triphenyl phosphine, palladium, triphenyl phosphine tetrakis, and phenyl phosphine tetrakis, and bis(triphenyl phosphine) palladium chloride complex. The acid acceptor is generally a tertiary amine. In general, the reaction vessel is pressurized with carbon monoxide to a pressure of between atmospheric and 3000 psi, preferred pressures are between 600 and 1000 psi.

This process is preferably run at a temperature of between 100° C. and 140° C., most preferably between 120° C. and 130° C. The hydrocarbyloxycarbonyl arylcyclobutene can be recovered by filtering off the catalyst, washing away the acid scavenger with a 10 percent strong acid solution, stripping off the solvent and distilling the product to purify it. To prepare a carboxyamide-substituted arylcyclobutene, a primary or secondary amine is substituted for the alcohol solvent. In the embodiment wherein the aryl radical is a benzene radical, the process corresponds to the following equation:

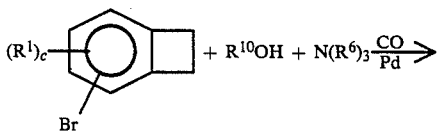

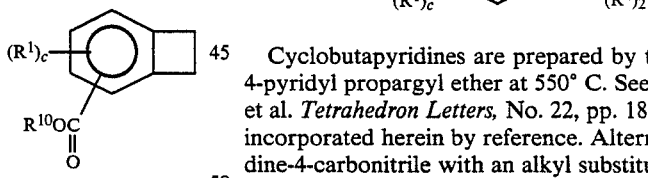

wherein $R^1$ and c are as hereinbefore defined and $R^6$ and $R^{10}$ are hydrocarbyl moieties. The hydrocarbyloxycarbonyl-substituted or carboxamide-substituted arylcyclobutenes can thereafter be acidified and converted to acid chlorides by the process described hereinbefore.

In another preparation of an arylcyclobutene, the reaction may follow that reported by Skorcz and Kaminski, *Org. Syn.*, 48, pages 53–56 (1968). In a typical preparation, an alkyl cyanoacetate is added to a solution of sodium metal in ethanol followed by the addition of an ortho-halomethylaryl halide. The alkyl 2-(O-halomethylaryl)cyanoacetate is isolated and treated with aqueous sodium hydroxide. Subsequent acidification results in the cyanoacetic acid derivative. That derivative is placed into N,N-dimethylformamide and is refluxed to form the 3-(O-halomethylaryl)propionitrile derivative which is isolated and added to a suspension of sodamide in liquid ammonia. After an appropriate reaction time, ammonium nitrate is added and the ammonia allowed to evaporate. The cyanoarylcyclobutene is isolated by ether extraction and purified by fractional distillation under reduced pressure.

Substituted arylcyclobutenes can be prepared by the same technique by using the appropriately substituted reactants, such as an alkyl or alkoxybenzyl halide. Also substituents can result from using an alkyl haloacetate or a dialkylmalonate.

In another preparation based on the paper by Matsura et al., *Bull. Chem. Soc. Jap.*, 39, 1342 (1966), o-aminoaryl carboxylic acid is dissolved in ethanol and hydrochloric acid added. Isoamylnitrite is slowly added to the cold stirred solution and diethyl ether is then added. The product, aryldiazonium-2-carboxylate hydrochloride, is filtered. That product is placed in a solvent, preferably ethylene dichloride, and acrylonitrile and propylene oxide is added to the stirred mixture which is then heated under nitrogen until the reaction is complete. After cooling, the mixture is filtered and the product, 1-cyanoarylcyclobutene, is isolated by fractionally distilling the filtrate under reduced pressure.

Amounts of reactants, reaction parameters and other details can be found in the cited article, the examples of this application, or can be easily deduced therefrom.

In a next sequence of reactions, the cyanoarylcyclobutene or substituted derivative is nuclear substituted. In one preparation, the cyanoarylcyclobutene is added slowly to a cold solution of sodium nitrate in concentrated sulfuric acid to form 5-nitro-1-cyanoarylcyclobutene. That nitro compound is isolated, dissolved in ethanol and reduced by hydrogenation over a palladium on carbon catalyst. The isolated product is 5-amino-1-cyanoarylcyclobutene. In the preferred embodiment where the aryl radical is benzene, the product corresponds to the formula Cyclobutapyridines are prepared by the pyrolysis of 4-pyridyl propargyl ether at 550° C. See J. M. Riemann et al. *Tetrahedron Letters*, No. 22, pp. 1867–1870 (1977), incorporated herein by reference. Alternatively, a pyridine-4-carbonitrile with an alkyl substituent on the carbon atom adjacent to the nitrile is reacted with sodium azide and ammonium chloride in N,N-dimethylformamide to prepare a 5(alkyl-4-pyridyl)tetrazole. The 5(alkyl-4-pyridyl)tetrazole is pyrolyzed at about 600° C. to prepare a cyclobutapyridine. See. W. D. Crow et al. *Australian Journal of Chemistry* 1741 et seq. (1975) incorporated herein by reference.

Amino cyclobutapyidines are prepared by reacting a cyclobutapyridine with sodamide ($NaNH_2$) in N,N-dimethylaniline solvent at 110° C. A hydroxycyclobutapyridine is prepared by reacting one mole of an aminocyclobutapyridine wih one mole of sodium nitrite and two moles of sulfuric acid in water at 0° C. for a period of time and thereafter warming to 50° C. Halosubstituted cyclobutapyridine is prepared by reacting a hydroxypyridine in thionyl at reflux either neat or in solution, for example, thionyl chloride or thionyl bromide, in N,N-dimethylformamide solvent.

The N-substituted arylcyclobutenyl-unsaturated cyclic imides of this invention wherein the bridging member is a direct bond can be prepared by the following method. An unsaturated cyclic anhydride is contacted with an amine-substituted arylcyclobutene under conditions so as to form an N-arylcyclobuteneylamido alkenoic acid. Such acid can thereafter be dehydrated to cyclize the amido alkenoic acid into a cyclic imide ring and form the N-substituted arylcyclobutenyl-unsaturated cyclic imide.

The formation of the arylcyclobutenyl amido alkenoic acid is achieved by reacting an unsaturated cyclic anhydride with an amine-substituted arylcyclobutene. This reaction is exemplified in one preferred embodiment wherein the anhydride is maleic anhydride and the arylcyclobutene is 5-aminobenzocyclobutene, and is illustrated by the following equation:

FORMULA 2

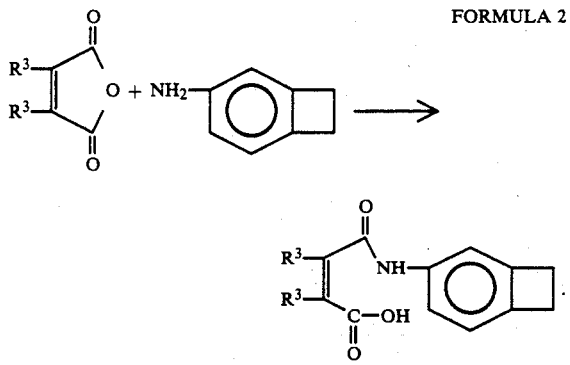

The cyclic anhydride and amino-substituted arylcyclobutene are contcated in a suitable solvent at a temperature of between −40° C. and 100° C. Suitable solvents include aliphatic hydrocarbons, aromatic hydrocarbons, ethers and halogenated hydrocarbons. It is preferred to run the process under an inert atmosphere. It is also preferred to use freshly sublimed anhydride as any impurities in the anhydride can result in very poor yields. It is also preferred to use at least a 5 percent excess of anhydride so as to drive the reaction to completion with respect to the amino-substituted arylcyclobutene compound.

Preferred temperatures are between 0° C. and 50° C. with between 20° C. and 25° C. being most preferred.

The N-arylcyclobutenylamido alkenoic acid can thereafter be dehydrated by one of two methods. In the preferred embodiment, the N-arylcyclobutenylamido alkenoic acid is contacted with a dehydrating agent in an aprotic reaction medium in the presence of a nickel II salt catalyst. In general, the reaction medium is an aprotic solvent and can include ketones, ethers, amides or aliphatic halogenated hydrocarbons. Preferred reaction media include the ketones, with acetone being most preferred. The dehydrating agents include anhydrides, carbodiimides and isocyanates; with the anhydrides being preferred and acetic anhydride being most preferred.

The catalyst is any nickel II salt with nickel II acetate being most preferred. In general, between about 1 and 5 percent of the catalyst is useful. It is preferable to run this process in the presence of an aprotic base such as a carbonate or tertiary amine, preferably a tertiary amine. In general, between about 20 and 200 mole percent of a tertiary amine is used, with between about 100 and 150 mole percent being preferred, wherein mole percentages are based on the starting N-arylcyclobutenylamido alkenoic acid. The mole ratio of the dehydrating agent to the N-arylcyclobutenylamido alkanoic acid is between about 4:1 and 1:1, preferably between about 1.5:1 and 1:1.

It is preferred to run this process under an inert atmosphere. Temperatures which are useful are those at which the dehydration takes place. Preferable temperatures are between about −20° C. and 100° C., with between about 15° C. and 25° C. being most preferred.

In this reaction, the N-arylcyclobutenylamido alkenoic acid is not soluble in the reaction medium but the cyclic imide product is soluble. The reactant is slurried in the reaction media and exposed to the reaction conditions described. The completion of the reaction is noted by dissolution of the reactants indicating formation of products.

In an alternative procedure, the N-arylcyclobutenyl amido alkenoic acid can be dehydated by dispersing the compound in a glacial acetic acid reaction media in the presence of an alkali or alkaline earth metal acetate salt, and heating the reaction mixture to a temperature at which the dehydration takes place to form the cyclic imide rings. Generally, a sufficient amount of alkali or alkaline earth metal acetate salt to cause complete dehydration is suitable. Preferably, at least an equimolar amount of alkali or alkaline earth metal acetate salt is used, most preferably an excess of 5 mole percent. The process can be run at any temperature at which the dehydration takes place, preferable temperatures are between 50° C. and 140° C., with between about 100° C. and 120° C. being most preferred. Completion of the reaction is indicated by dissolution of the product.

In both instances, the product can be recovered by washing with water and thereafter an aqueous solution of an inorganic base.

To prepare an N-substituted arylcyclobutenyl cyclic imide with a hydrocarbylene amido, hydrocarbyleneoxy or hydrocarbyleneoxycarbonyl bridge, an unsaturated cyclic anhydride is reacted with a hydrocarbon substituted with amino and carboxyl moieties, for the hydrocarbylene amido-bridged species, or a hydrocarbon substituted with amino and hydroxyl moieties, for the hydrocarbyleneoxy and hydrocarbyleneoxycarbonyl-bridged species, to prepare an amido alkanoic acid wherein the amido nitrogen is substituted with a carboxy-substituted hydrocarbyl or hydroxy-substituted hydrocarbyl moiety. This reaction can be performed at a temperature of between −40° C. and 100° C. in a suitable solvent. Suitable solvents include aliphatic hydrocarbons, aromatic hydrocarbons, ethers and halogenated hydrocarbons. It is preferred to run the process under an inert atmosphere. It is preferred to use freshly sublimed anhydride as any impurities can result in very poor yields. It is preferred to use at least a 5 percent excess of anhydride so as to drive the reaction to completion.

In the embodiment wherein the anhydride is maleic anhydride, these reactions are exemplified by the following equations

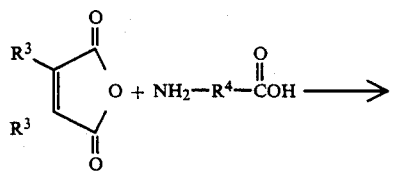

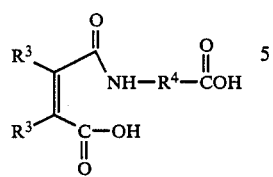

and

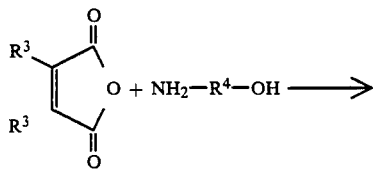

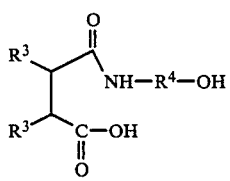

wherein $R^3$ is as hereinbefore defined and $R^4$ is a hydrocarbylene radical.

The amido alkenoic acid can be dehydrated using one of the two dehydration methods described hereinbefore so as to prepare a N-substituted cyclic imide wherein the substituent is a N-hydrocarbylcarbonyloxycarbonyl cyclic imide, or a N-hydrocarbylcarbonyloxy cyclic imide. In the embodiment wherein the N-substituted amido alkenoic acid was derived from maleic anhydride, this reaction is exemplified by the following equations

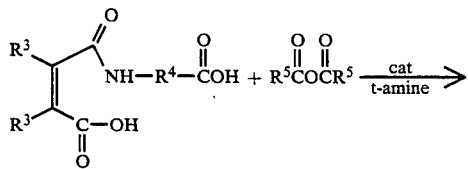

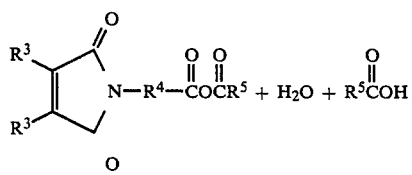

and

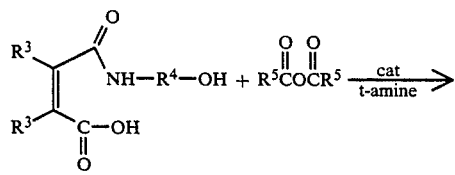

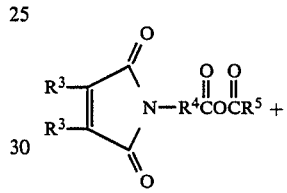

wherein $R^3$ and $R^4$ are as hereinbefore defined and $R^5$ is a hydrocarbyl moiety.

The N-hydrocarbylcarbonyloxycarbonyl cyclic imide is converted to a hydrocarbylene amido-bridged N-substituted arylcyclobutenyl cyclic imide by reacting the N-hydrocarbylcarbonyloxycarbonyl cyclic imide with an amino-substituted arylcyclobutene in the presence of a tertiary amine. This process can be accomplished by contacting the starting reactants in a chlorinated aliphatic hydrocarbon solvent at about 0° C. with agitation under an inert atmosphere. This process is exemplified by the following equation

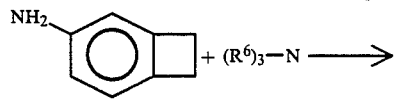

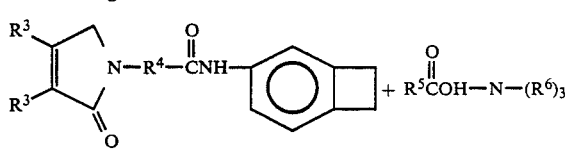

wherein $R^4$ and $R^5$ are as hereinbefore defined, and $R^6$ is a hydrocarbyl radical.

To prepare a hydrocarbyleneoxy or hydrocarbyleneoxycarbonyl-bridged N-substituted arylcyclobutenyl cyclic imide, the N-hydrocarbylcarbonyloxyhydrocarbyl cyclic imide is hydrolyzed to prepare a N-hydroxyhydrocarbyl cyclic imide. The hydrolysis is usually run in an aqueous/alkanol solvent system in the presence of an acid or base catalyst at between room temperature and reflux of the solvent mixture (about 20° C. to 60° C.). This reaction is exemplified by the following equation

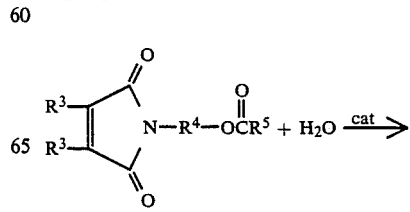

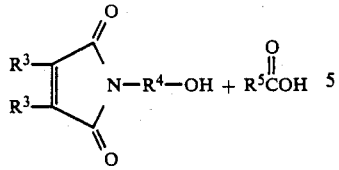
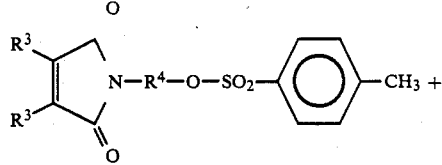

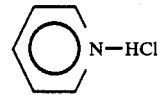

wherein $R^3$, $R^4$ and $R^5$ are as hereinbefore defined.

To prepare the hydrocarbyleneoxycarbonyl-bridged N-substituted arylcyclobutenyl cyclic imides, the N-hydroxyhydrocarbyl cyclic imide is reacted with a chlorocarbonyl-substituted arylcyclobutene. In practice, the N-hydroxyhydrocarbyl cyclic imide is dissolved in a chlorinated aliphatic hydrocarbon solvent to which is added a tertiary amine, which functions as an acid acceptor, and thereafter the chlorocarbonyl-substituted arylcyclobutene in a chlorinated aliphatic hydrocarbon is added slowly to the mixture. This is preferably done at about 0° C. in an inert atmosphere. It is preferred to stir the reaction mixture for a period of time at 0° C. after the addition is complete. This reaction is exemplified by the following equation

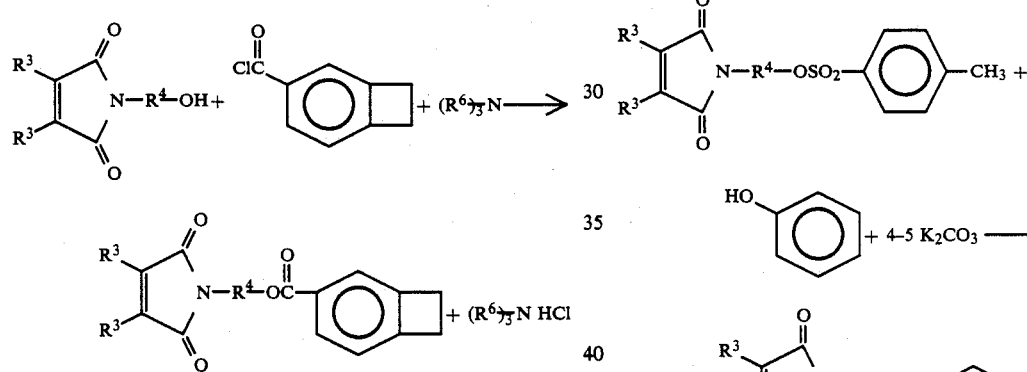

wherein $R^3$, $R^4$ and $R^6$ are as hereinbefore defined.

The hydrocarbyleneoxy-bridged N-substituted arylcyclobutenyl cyclic imides can be prepared from the N-hydroxyhydrocarbyl cyclic imide in the following manner. The N-hydroxyhydrocarbyl cyclic imide is reacted with p-toluene sulfonyl chloride and pyridine to prepare a cyclic imido hydrocarbyl p-toluene sulfonate. Either excess pyridine or methylene chloride are used as the solvent. The reactants are contacted in equimolar amounts, unless pyridine is the solvent, at a temperature of between about 0° C. and 25° C. This reaction is exemplified by the following equation

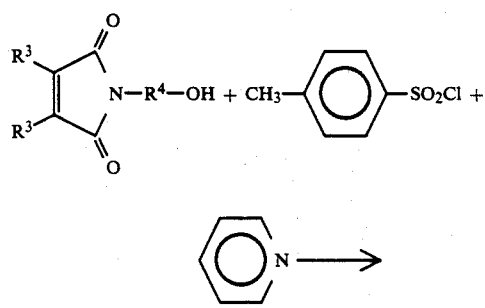

wherein $R^3$ and $R^4$ are as hereinbefore defined.

The cyclic imido hydrocarbyl p-toluene sulfonate is contacted with a hydroxy-substituted arylcyclobutene in the presence of a four to five molar excess of an alkali metal carbonate (such as potassium carbonate) based on the sulfonate, in a N,N-dimethyl formamide solvent, to prepare a hydrocarbyloxy-bridged N-substituted arylcyclobutenyl cyclic imide. This reaction takes place at temperatures of between about 20° C. and 140° C. This process is exemplified by the following equation wherein $R^3$ and $R^4$ are as hereinbefore defined.

The hydrocarbylene amino-bridged N-substituted arylcyclobutenyl cyclic imides can be prepared by the following procedure. An amino-substituted arylcyclobutene is reacted with about an equimolar amount of a hydrocarbon substituted with aldehyde and nitro moieties, in the presence of between about 0.3 to 1.5 moles of sodium cyanoborohydride in a methanolic solvent at about 20° C. to about 25° C. The product is nitrohydrocarbyl amino-substituted arylcyclobutene. The process can be exemplified by the following equation

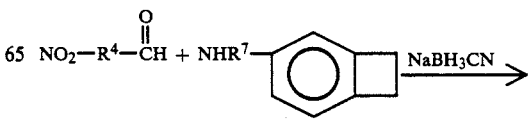

-continued

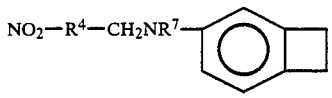

wherein $R^4$ is as hereinbefore defined and $R^7$ is hydrogen or a hydrocarbyl moiety. The nitro moiety on the nitrohydrocarbyl amino-substituted arylcyclobutene is reduced to an amine moiety by contacting with an excess of metallic zinc in a concentrated hydrochloric acid solution at between about 20° C. and reflux. The product corresponds to the formula

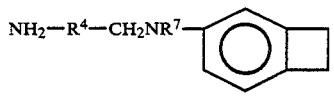

wherein $R^4$ is as hereinbefore defined. The aminohydrocarbyl amino-substituted arylcyclobutene is thereafter reacted with an unsaturated cyclic anhydride to prepare a hydrocarbylene amino-bridged N-arylcyclobutenyl amido alkenoic acid. The conditions for this reaction are as described hereinbefore for the reaction of an amino-substituted arylcyclobutene and a cyclic anhydride. This reaction is exemplified by the following equation

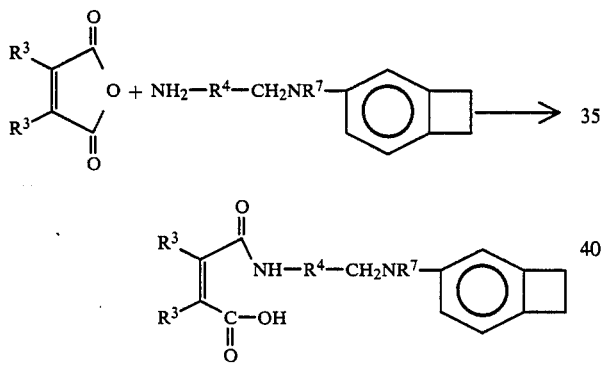

The hydrocarbylene amino-bridged N-aryl cyclobutenyl amido alkenoic acid is thereafter dehydrated by one of the methods described hereinbefore to prepare the hydrocarbylene amino-bridged N-substituted arylcyclobutenyl cyclic imide. This product corresponds to the formula

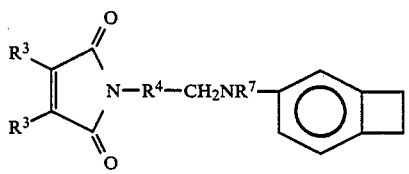

wherein $R^4$ and $R^7$ are as hereinbefore defined.

A hydrocarbylene-bridged N-substituted arylcyclobutenyl cyclic imide can be prepared by the following procedure. A carboxy-substituted or carboxyhydrocarbyl-substituted arylcyclobutene is reduced to a hydroxyhydrocarbyl-substituted arylcyclobutene by reacting the starting material with about a 3:1 molar excess of diborane in an ether or cyclic ether solvent at between about 0° C. to 20° C. This process is exemplified by the following equation

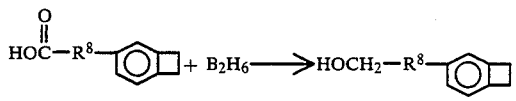

wherein $R^8$ is a direct bond or a hydrocarbylene moiety. The hydroxyhydrocarbyl-substituted arylcyclobutene is reacted with a slight excess of thionyl chloride to prepare a chlorohydrocarbyl-substituted arylcyclobutene. The reactants are usually contacted neat or in a methylene chloride solvent at a temperature of between about 0° C. and 50° C. An example of the product corresponds to the formula

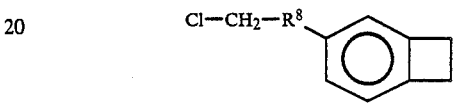

The chlorohydrocarbyl-substituted arylcyclobutene is thereafter reacted with about an equimolar amount of potassium phthalamide to prepare an N-arylcyclobutenylhydrocarbyl phthalamide. The reactants are generally contacted neat at temperatures of between about 100° C. and 200° C. This reaction is exemplified by the following equation

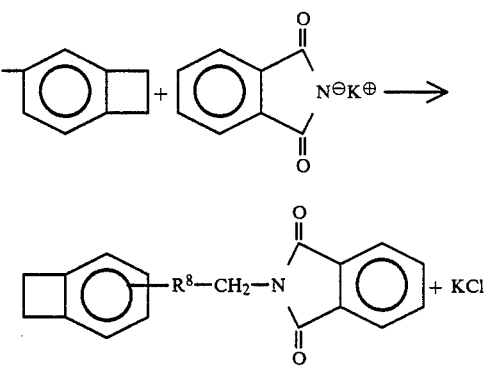

wherein $R^8$ is as hereinbefore defined. The N-arylcyclobutenylhydrocarbyl phthalamide is reacted with about one equivalent of hydrazine hydrate to prepare an aminohydrocarbyl-substituted benzocyclobutene. The reactants are contacted in an alkanol solvent at the reflux of the solvent. The product corresponds to the formula

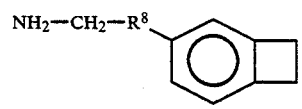

wherein $R^8$ is as hereinbefore defined. The aminohydrocarbyl-substituted benzocyclobutene is thereafter reacted with an unsaturated cyclic anhydride to prepare an N-hydrocarbylarylcyclobutenyl amido alkenoic acid under the conditions described hereinbefore. This process is exemplified by the following equation

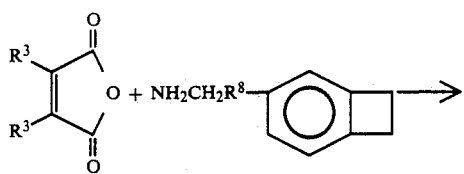

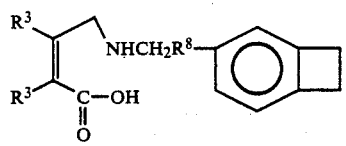

wherein $R^3$ and $R^8$ are as hereinbefore defined. The N-hydrocarbylarylcyclobutenyl amido alkenoic acid is then dehydrated to form a cyclic imide ring thus preparing an N-hydrocarbylarylcyclobutenyl cyclic imide. This process is performed using one of the two dehydration processes described hereinbefore.

To prepare a mercaptoarylcyclobutene, an arylcyclobutene sulfonic acid and equimolar amounts of sodium hydroxide are contacted in aqueous solution at about 20° C.–25° C. to prepare sodium arylcyclobutene sulfonate. The sodium arylcyclobutene sulfonate is dried at 100° C., and thereafter contacted in neat form with about 0.48 mole of phosphorous pentachloride at about 170° C. to 180° C. to prepare an arylcyclobutene sulfonyl chloride. The arylcyclobutene sulfonyl chloride is reduced with zinc, about 4.9 moles, in the presence of about 6.8 moles of concentrated sulfuric acid at about 0° C. to prepare the mercaptoarylcyclobutene.

To prepare the alkylenethio-bridged N-substituted arylcyclobutenyl-unsaturated cyclic imide, equimolar amounts of a mercapto arylcyclobutene, sodium hydroxide and a dihaloalkane are contacted in the alkanol solvent at between about 0° C. and 50° C. The product is a haloalkyl-subtituted arylcyclobutenyl sulfide. This reaction is exemplified by the following equation

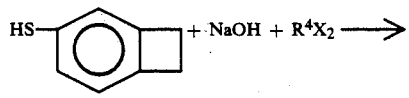

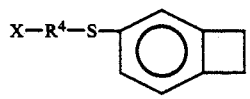

wherein X is halogen and $R^4$ is a divalent alkane radical. Two moles of the haloalkyl-substituted arylcyclobutenyl sulfide is contacted with about 0.8 moles of potassium phthalimide and about 0.4 mole of potassium carbonate. The reactants are contacted neat at a temperature of about 190° C. to prepare an n-phthalimidoalkyl arylcyclobutenyl sulfide. This process is exemplified in one preferred embodiment by the following equation

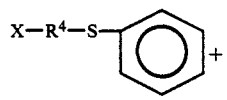

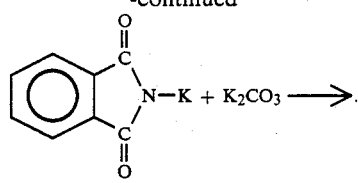

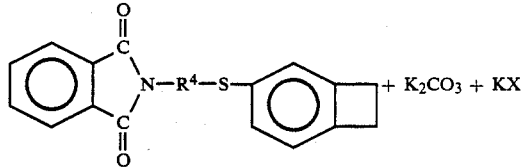

The phthalimidoalkyl arylcyclobutenyl sulfide is contacted with a hydrazine hydrate in a mole ratio of about 1 to 1.25, respectively, in an alkanol solvent at reflux to prepare an aminoalkyl arylcyclobutenyl sulfide. In one preferred embodiment, the product corresponds to the formula

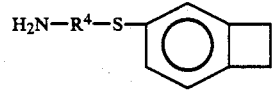

The aminoalkylarylcyclobutenyl sulfide is then reacted with an unsaturated cyclic anhydride to prepare a thioalkylene-bridged N-aryl cyclobutenyl aminoalkenoic acid. This is achieved under conditions described hereinbefore. Thereafter, the alkylenethio N-arylcyclobutenyl amidoalkenoic acid can be dehydrated by one of the methods described hereinbefore to prepare an alkylenethiobridged N-substituted arylcyclobutenyl cyclic imide.

To prepare arylenethio-bridged N-arylcyclobutenyl cyclic imide, equimolar amounts of a mercapto arylcyclobutene, sodium hydroxide and a halonitro-substituted aromatic compound are contacted in an alkanol solvent under reflux to prepare a nitroaryl arylcyclobutenyl sulfide. The nitro group on the nitroaryl arylcyclobutenyl sulfide is reduced by contacting one mole of such compound with about two moles of tin and about six moles of concentrated hydrochloric acid to prepare an aminoaryl arylcyclobutenyl sulfide. The aminoaryl arylcyclobutenyl sulfide is thereafter contacted with a an unsaturated cyclic anhydride in equimolar amounts in methylene chloride at a temperature of about 0° C. to about 25° C. to prepare an arylenethio-bridged N-arylcyclobutenyl amidoalkenoic acid. The arylenethio-bridged N-arylcyclobutenyl amidoalkenoic acid is dehydrated using procedures described hereinbefore to prepare an arylenethio-bridged N-arylcyclobutenyl cyclic imide.

The hydrocarbylenethio-bridged N-arylcyclobutenyl cyclic imides can be contacted with equimolar amounts of peracetic acid in an ethyl acetate solvent at between about 0° C. to 20° C. to prepare a hydrocarbylenesulfinyl-bridged N-arylcyclobutenyl cyclic imide. The hydrocarbylenethio-bridged N-arylcyclobutenyl cyclic imide can be contacted with about 2 moles of peracetic acid for each mole of the bridged cyclic imide in ethyl acetate solvent at about 0° C. to 20° C. to prepare a hydrocarbylenesulfonyl-bridged N-arylcyclobutenyl cyclic imide.

To prepare the various bridged N-arylcyclobutenyl cyclic imides wherein the aryl moiety is a heterocycle, the appropriately substituted heterocyclic N-arylcyclobutenyl cyclic imide is reacted in the manner described herein to get the appropriately desired compound.

The compounds of this invention are unique in several respects. They have intramolecular diene and dienophile functionality. They are thermally stable for long periods at elevated temperatures, up to 100° C. They are readily polymerizable. The compounds of this invention are useful in the preparation of polyimides by polymerization of one or more of the compounds of this invention. It is believed that the polymerization takes place by a Diels-Alder reaction wherein the unsaturation on the cyclic imide acts as a dienophile while the cyclobutene ring forms a diene which reacts with the dienophile to form the polymeric compositions.

The polymers of this invention are prepared by heating the compounds described hereinbefore to a temperature of 170° C. or greater. Preferable temperatures for polymerization are 200° C. or greater. In general, it is preferable to run the polymerization at a temperature of between about 170° C. and 300° C., with between about 200° C. and 300° C. being most preferred.

Wherein the N-substituted arylcyclobutenyl cyclic imides correspond to the formula

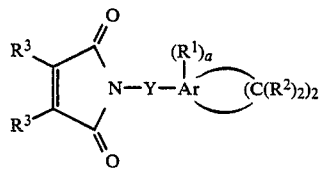

wherein Ar, $R^1$, $R^2$, $R^3$, Y and a are as described hereinbefore; it is believed that the polymeric composition contains units which correspond to the formula

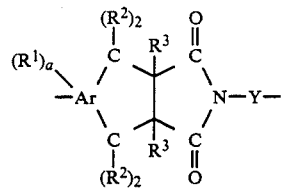

It is further believed that in one preferred embodiment of the polymers derived from monomers of such a formula result in the preparation of polymers which correspond generally to the formula

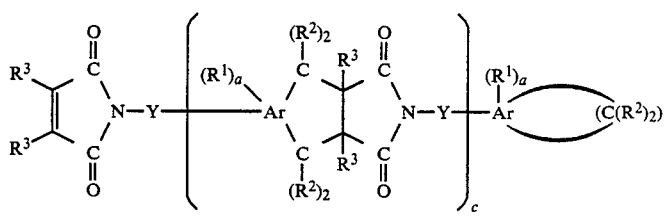

wherein Ar, $R^1$, $R^2$, $R^3$, Y and a are as described hereinbefore and c is a real number of about 2 or greater, and most preferably 20 or greater.

In another preferred embodiment, the polymeric composition is the polymer of one or more compounds which corresponds to the formula

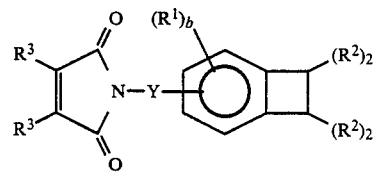

wherein $R^1$, $R^2$, $R^3$, Y and b are as hereinbefore defined. In this embodiment, it is believed that the polymer prepared contains units which correspond to the formula

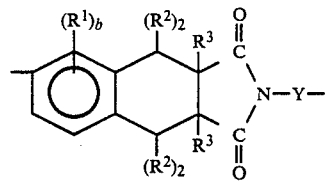

wherein $R^1$, $R^2$, $R^3$, Y and b are as hereinbefore defined.

In one preferred embodiment wherein the compound or compounds polymerized corresponds to said formula, it is believed that the polymer prepared corresponds to the formula

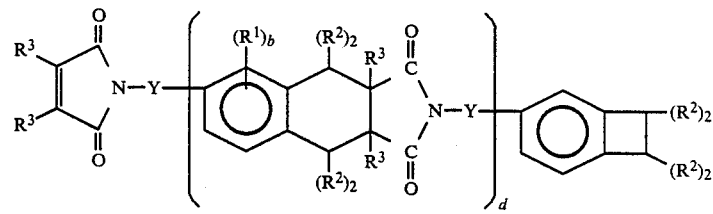

wherein $R^1$, $R^2$, $R^3$, Y and b are as hereinbefore defined, and d is a real number of about 2 or greater. d is preferably about 20 or greater.

The novel N-substituted arylcyclobutenyl-unsaturated cyclic imide compounds of this invention are useful in the preparation of polymeric compositions. In general, these polymeric compositions are prepared by contacting these N-substituted arylcyclobutenyl-unsaturated cyclic imide compounds and heating them to the polymerization temperature of the particular monomer used. The polymerization is an addition polymerization wherein no volatiles are generated. Furthermore, no catalyst initiator or curing agents are necessary for the polymerization to take place. It is believed that the polymerization takes place when the cyclobutene ring undergoes transformation to prepare an aryl radical with two olefinic unsaturated moieties ortho to one another wherein the olefinic unsaturated moieties thereafter undergo reaction with the unsaturated cyclic imide moieties. It is to be noted that the temperature at which polymerization is initiated is dependent upon the nature of substituents on the cyclobutene ring. In general, wherein the cyclobutene ring is unsubstituted, the polymerization is initiated at about 200° C. Wherein the cyclobutene ring is substituted with an electron-donating substituent, the polymerization temperature is generally lowered, the higher the ability of the substituent to donate electrons, the lower the polymerization initiation temperature is.

The method of polymerization of the N-substituted arylcyclobutenyl-unsaturated cyclic imide monomers has a significant effect on the nature and properties of the polymeric composition prepared. In one embodiment, the N-substituted arylcyclobutenyl-unsaturated cyclic imide monomers of this invention can be melt polymerized. The melt polymerization of N-substituted arylcyclobutenyl-unsaturated cyclic imide monomers allows their use in the preparation of solid parts, as coatings, in composites, as adhesives and as fibers.

In one embodiment of the melt polymerization, the monomers are heated to the temperature at which it melts, preferably this is a temperature of between about 80° C. and 100° C., and thereafter poured or injected into a mold. Thereafter, pressure may be applied on the melted monomer in the mold. Generally, pressures of between about atmospheric and 2000 psi are suitable. Thereafter, the monomer is heated to a temperature at which the monomers undergo polymerization. This is preferably a temperature of between about 200° C. and 300° C., more preferably between about 200° C. and 250° C. for between about 10 minutes and 3 hours. Upon cooling, the polymerized composition can be removed from the mold.

Polymers prepared in this manner can subsequently be thermally treated at temperatures above 200° C. to raise the modulus and lower the coefficient of expansion of such polymeic compositions.

In general, the polymers prepared by this method are insoluble in that they swell but do not dissolve, are thermally stable at 200° C., have a good modulus, a low water pickup and are reasonably hard.

In another embodiment, the N-substituted arylcyclobutenyl-unsaturated cyclic imide monomers of this invention can be used to prepare coatings and films. In such embodiments, the monomers are dissolved in a suitable solvent and coated onto the substrate of choice, and thereafter the coated substrate is exposed to temperatures at which the monomers undergo polymerization over a period of time sufficient for the polymerization to go to completion. Under preferable conditions, temperatures of above about 200° C. for between 1 and 5 hours are used. Suitable solvents are those which volatilize away at temperatures below the polymerization temperature. Preferred solvents are cyclic and aliphatic ethers, lower alkanols, amides, and chlorinated hydrocarbon solvents. It is preferable to saturate the solvent with the monomer, a 20 to 30 weight percent concentration of monomer in the solvent is preferred.

The N-substituted arylcyclobutenyl-unsaturated cyclic imide monomers may be combined with the powder-form or fibrous fillers or reinforcing materials either before or after heat treatment. For example, it is possible to impregnate powder-form or fibrous fillers or reinforcing materials such as quartz sand or glass cloths, with the N-substituted arylcyclobutenyl-unsaturated cyclic imide monomers, optionally in solution.

Suitable fillers and reinforcing materials are, generally, in any powder form and/or fibrous products, for example, of the type commonly used in the production of moldings based on unsaturated polyester resins or epoxide resins. Examples of products such as these are, primarily, granular fillers such as quartz powder, ground shale, asbestos powder, powdered corundum, chalk, iron powder, aluminum powder, sand, gravel and other fillers of this kind, also inorganic or organic fibers, more especially glass fibers in the usual textile forms of fibers, filaments rovings, yarns, nonwovens, mats and cloths, etc. In this connection, amino silane-based finishes have proven to be particularly effective. It is also possible to use corresponding textile structures of organic, preferably synthetic fibers (polyamides, polyesters) or on the basis of quartz, carbon, metals, etc., as well as monocrystals (whiskers).

The end products combined with fillers or reinforcing materials may be used in particular in vessel and pipe construction by the winding technique, in electrical engineering, in mold construction and tool making and also in the construction of heavily stressed components, in the lightweight construction of vehicles in aeronautical and astronautical engineering.

In another embodiment, the N-substituted arylcyclobutenyl-unsaturated cyclic imide monomers can be used as adhesives. In such embodiment, one of the substrates to be joined is contacted with some form of the monomers, for example, the monomer in a powdered form. Thereafter, the second substrate to be adhesivated is contacted with the substrate previously contacted with the monomer where the monomer was contacted with the first substrate. Thereafter, pressure of at least 1 psi is applied and the monomers and substrates are raised to a temperature at which the monomer undergoes polymerization.

In one embodiment, the N-substituted arylcyclobutenyl-unsaturated cyclic imide monomers can be formed into a prepolymer which thereafter can be polymerized. To form the prepolymer, the N-substituted arylcyclobutenyl-unsaturated cyclic imide monomers are contacted in an inert atmosphere or under vacuum and heated to a stage at which the polymerization mixture is sufficiently viscous enough to be moldable in conventional molding equipment. In general, the monomers can be contacted at a temperature of 190° C. to 220° C. for between about 1 and 10 minutes. Thereafter, the prepolymer can be used in various techniques to prepare the polymeric compositions of this invention. In one preferred embodiment, the prepolymer is cooled to form a powder which can be used to form compression molded articles, as an adhesive, and in many other uses. In another embodiment, a prepolymer of the N-substituted arylcyclobutenyl-unsaturated cyclic imide monomers can be prepared by precipitation polymerization. In particular, the technique involves heating such monomers in a solvent to prepare a low molecular weight prepolymer that contains unreacted arylcyclobutene rings. A solvent is used which dissolves the monomer but not the prepolymer. As the prepolymer forms, it precipitates and is removed. The prepolymer can be fabricated in a hot compression mold which reacts out the remaining arylcyclobutene rings to give a thermoset polymer. The product is a fine white powder.

Preferable solvents are nonpolar solvents, such as aromatic hydrocarbons, aliphatic hydrocarbons, aliphatic chlorinated hydrocarbons, aromatic chlorinated hydrocarbon solvents, biphenols, naphthalenes or polychlorinated biphenols. The polymerization can take place at temperatures generally of between about 200° C. and 240° C. for periods of between about 1 and 5 hours. In general, the monomer can be dissolved up to saturation in the solvent used. A 20 to 30 percent by weight solution of the monomer in the solvent is preferred.

In another embodiment, the N-substituted arylcyclobutenyl-unsaturated cyclic imide monomers can be polymerized by solution polymerization techniques. In this embodiment, the monomers are dissolved in dipolar aprotic solvents with boiling points above the polymerization temperature of the monomers. It is preferable that the solvents have a boiling point of above 200° C. and more preferable that the solvents have a boiling point of above 250° C. Examples of preferred dipolar aprotic solvents include amides and sulfones. It is necessary to add to the solution lithium salts which solubilize the monomer in the solvents, preferably between about 5 and 20 weight percent based on the monomer. A preferred lithium salt is lithium chloride. The polymerization takes place by heating the polymerization solution to a temperature at which the monomer undergoes polymerization, preferably above 200° C. The polymerization time is generally between about 1 and 10 hours. The polymer can be recovered by adding water to precipitate the polymer from the reaction solution and thereafter stripping off the solvent. The polymers prepared with this method can be used in compression moldings or to prepare coatings. It is often desirable to process these polymers under elevated temperatures.

In another embodiment, the monomers of this invention which undergo polymerization at a temperature which is below the melting point of the monomer can be polymerized in a solid state polymerization. In this method, the monomers are heated to a temperature at which polymerization takes place. Polymers prepared in this method can be useful in the preparation of bearings, seals and other parts by powder metallurgy techniques.

Specific Embodiments

The following examples are included to illustrate the invention, and do not limit the scope of the invention or the claims. Unless otherwise specified, all parts and percentages are by weight.

EXAMPLE 1

(a) Preparation of Ethyl 2-(o-Chlorobenzyl) Cyanoacetate

Into a 3-liter, three-necked flask equipped with a mechanical stirrer, reflux condenser, addition funnel and nitrogen inlet is placed a solution of 35.64 g (1.55 moles) of sodium metal in 1050 mm of absolute 2B ethanol. The solution is stirred under nitrogen and cooled to 0° C. in an ice bath and 763.56 g (6.75 moles) of ethyl cyanoacetate is added dropwise over a period of 15 minutes. To this white suspension is added 241.56 g (1.5 moles) of o-chlorobenzyl chloride dropwise over 1 hour. After the addition is complete, the ice bath is removed and the mixture is slowly heated under nitrogen to reflux and held there for 3 hours. The resulting pink-colored mixture is allowed to cool under nitrogen overnight at room temperature. About 1 liter of ethanol is distilled from the reaction mixture and 1.5 liters of water are added. The organic layer is taken up in three 400-ml portions of methylene chloride, and the solutions are combined and washed once with 150 ml of water. The methylene chloride solution is dried over anhydrous magnesium sulfate, filtered and evaporated on a rotary evaporator. The residual liquid is distilled under reduced pressure through an insulated 12-inch Vigreux column. A forerun of ethyl cyanoacetate (boiling point 55° C.–60° C./0.3 mm Hg) comes over first followed by pure ethyl 2-(o-chlorobenzyl)cyanoacetate. The infrared, $^1$H and $^{13}$C nuclear magnetic resonance are used to establish the structure. The yield is 68 percent of product having a boiling point of 130° C.–135° C./0.3 mm Hg.

(b) Preparation of 2-(o-Chlorobenzyl)Cyanoacetic Acid

In a 2-liter, three necked flask equipped with a mechanical stirrer, addition funnel and nitrogen inlet is placed 243 g (1.02 moles) of ethyl 2-(o-chlorobenzyl)cyanoacetate. A solution of 54.52 g (1.363 moles) of sodium hydroxide pellets and 545 ml of water is added over a period of 15 minutes while stirring under nitrogen. Initially, the solution turns cloudy and then becomes clear. The resulting mixture is stirred for 5 hours at room temperature under nitrogen. Water (445 ml) is added and the mixture is cooled in an ice bath. Acidifying to pH 1 with 4N hydrochloric acid gives a fine white precipitate that is filtered and washed with water until neutral to litmus. The product is dried in a vacuum oven at 60° C. overnight to yield 20 g (97 percent) of white powder. This material is recrystallized from toluene to give pure white crystals of 2-(o-chlorobenzyl)-cyanoacetic acid identified by infrared, $^1$H and $^{13}$C nuclear magnetic resonance. The yield is 94 percent of product having a melting point of 132° C.–134° C.

(c) Preparation of 3-(0-chlorophenyl) propionitrile

Into a 1-liter, three-necked flask equipped with a mechanical stirrer, reflux condenser and nitrogen inlet is placed 138.5 g (0.66 mole) of 2-(o-chlorobenzyl)-cyanoacetic acid and 220 ml of dry N,N-dimethylformamide. The mixture is stirred and slowly heated under nitrogen to reflux and held there for 6 hours. The resulting yellow mixture is allowed to cool under nitrogen overnight at room temperature. A precipitate (approximately 0.5 g) that forms is filtered off and the filtrate is poured into 1 liter of water. The organic layer is taken up in three 330-ml portions of ethyl ether/hexane (1:1 v/v), and the solutions are combined and washed once with 150 ml of water. The ethyl ether/hexane solution is dried over anhydrous magnesium sulfate, filtered and evaporated on a rotary evaporator. The residual liquid is distilled under reduced pressure through an insulated 12-inch Vigreux column with the product being collected at 82° C.–85° C./0.3 mm Hg as a colorless liquid identified by infrared, 'H and $^{13}$C nuclear magnetic resonance. The yield is 94.7 percent.

(d) Preparation of 1-Cyanobenzocyclobutene

A 3-liter, three-necked flask equipped with a dry ice condenser, mechanical stirrer and Claisen adapter fitted with an ammonia gas inlet and nitrogen inlet is rinsed with acetone, dried in an oven at 125° C., and heated with an air gun while flushing with nitrogen. The apparatus is cooled in a dry ice-acetone bath and the condenser is filled with a dry ice-acetone mixture. Ammonia gas flow is initiated and 600 ml is condensed out. The ammonia inlet tube is replaced by a stopper, and 0.4 g of powdered iron (III) nitrate is added. Sodium metal, 51.52 g (2.24 moles) is added in small portions over 1 hour. After all the sodium is added, the dry ice bath is removed and cooling is left to the dry ice condenser. Complete conversion of the sodium/ammonium solution to sodamide is indicated by a color change from deep blue to gray. Next, 92.82 g (0.56 mole) of 3-(o-chlorophenyl)propionitrile is added over a period of 10 minutes. The last traces of the nitrile are washed into the flask with small amounts of anhydrous ethyl ether. The dark green reaction mixture is stirred vigorously for 3 hours and then is treated with 134.4 g (1.68 moles) of solid ammonium nitrate. The ammonia is allowed to evaporate overnight at room temperature. Water (420 ml) is cautiously added to the residue. The organic layer is taken up in two 224-ml portions of chloroform, and the solutions are combined and washed twice with 140 ml of aqueous 5 percent hydrochloric acid and once with 140 ml of water. The chloroform solution is dried over anhydrous magnesium sulfate, filtered, and evaporated on a rotary evaporator. The residual liquid is distilled under reduced pressure through an insulated 12-inch Vigreux column. The product is collected at 59° C.–69° C./0.2 mm Hg. The infrared, 'H and $^{13}$C nuclear magnetic resonance are run to identify the product. The yield is 50 percent.

(e) Preparation of 5-nitro-1-cyanobenzocyclobutene

Into a 500-ml, three-necked flask equipped with an addition funnel, thermometer and nitrogen inlet is placed 14.1 g (0.17 mole) of sodium nitrate and 135 ml of concentrated sulfuric acid. The mixture is stirred under nitrogen while cooling to −5° C. (calcium chloride/ice) and 19.5 g (0.16 mole) of 1-cyanobenzocyclobutene is added dropwise at such a rate as to keep the reaction temperature below 2° C. The reaction mixture is then stirred under nitrogen at 0° C.–5° C. for 0.5 hour, poured onto 1050 g of ice, and extracted with four 300-ml portions of methylene chloride. The methylene chloride solutions are combined, washed with four 150-ml portions of 10 percent sodium bicarbonate, once with 300 ml of water, and dried over anhydrous magnesium sulfate. The methylene chloride solution is filtered and evaporated on a rotary evaporator to give 26.9 g of residue which is recrystallized from absolute 2B ethanol to give pure 5-nitro-1-cyanobezocyclobutene identified by infrared, 'H and $^{13}$C nuclear magnetic resonance. The melting point is 110° C.–112° C. and the yield is 64.1 percent.

(f) Preparation of 5-Amino-1-Cyanobenzocyclobutene

Into a 1-liter, three-necked flask equipped with a gas dipersion tube, reflux condenser, rubber septum and nitrogen inlet is placed 7 g (0.04 mole) of 5-nitro-1-cyanobenzocyclobutene and 400 ml of absolute 2B ethanol. The mixture is stirred under nitrogen and heat is applied to dissolve the solid. After adding 2.4 ml of glacial acetic acid and 1.6 g of 5 percent palladium on carbon, hydrogen flow is initiated and the mixture is hydrogenated at atmospheric pressure and ambient temperature. The hydrogenation is followed by thin-layer chromatography (silica gel; 70 percent toluene, 25 percent ethyl acetate, 5 percent triethylamine as eluent) and this shows the reaction is essentially complete in 1 hour. After 3 hours, the hydrogen flow is stopped and the system is purged with nitrogen for 15 minutes to remove excess hydrogen gas. The catalyst is removed by filtration using Celite and quickly quenched in water. The filtrate is evaporated to dryness on a rotary evaporator and the residue is treated with aqueous 10 percent sodium hydroxide. The aqueous solution is extracted with three 100-ml portions of ethyl ether, and the solutions are combined and washed once with 100 ml of water. The ethyl ether solution is dried over anhydrous potassium carbonate, filtered and evaporated on a rotary evaporator to give an amber-colored oil that solidified on standing. The product is pumped under vacuum overnight to remove the last traces of ethyl ether and stored under nitrogen. The infrared, 'H and $^{13}$C nuclear magnetic resonance are run. The yield is 86.4 percent.

(g) Preparation of N-[5-(1-Cyanobenzocyclobutenyl)]maleamic Acid

Into a 250-ml, three-necked flask equipped with a mechanical stirrer, addition funnel, reflux condenser, thermometer and nitrogen inlet is placed 4.9 g (0.05 mole) of freshly sublimed maleic anhydride and 50 ml of dry chloroform. The mixture is stirred under nitrogen while cooling to 15° C. in an ice bath and a solution of 7 g (0.05 mole) of 5-amino-1-cyanobenzocyclobutene in 50 ml of dry chloroform is added dropwise at such a rate as to keep the reaction mixture below 20° C. The reaction is maintained below 20° C. and stirred under nitrogen for 1 hour after addition is complete. The solid N-[5-(1-cyanobenzocyclobutenyl)]maleamic acid is filtered off, washed with cold chloroform, then with hot ethyl acetate/2B ethanol (absolute; 1:1 v/v), and dried overnight in a vacuum oven at 60° C. The infrared, 'H and $^{13}$C nuclear magnetic resonance, and carbon, hydrogen, nitrogen analyses are run.

| Analysis | Calculated | Found |
|---|---|---|
| carbon | 64.46 | 63.80 |
| hydrogen | 4.16 | 4.44 |
| nitrogen | 11.57 | 11.36 |

The yield is 11.32 g equal to 94.25 percent and the melting point is 190° C.–192° C.

(h) Preparation of N-[5-(1-Cyanobenzocyclobutenyl)]maleimide

Into a 250-ml, three-necked flask equipped with a mechanical stirrer, reflux condenser, thermometer and nitrogen inlet is placed 11 g (0.045 mole) of N-[5-(1-cyanobenzocyclobutenyl)]maleamic acid, 2.4 g (0.03 mole) of anhydrous sodium acetate, and 45.94 g (0.765 mole) of fresh glacial acetic acid. The mixture is stirred and slowly heated under nitrogen until a clear yellow solution results (117° C.–118° C.). After 5 minutes the heat is removed and the reaction mixture is allowed to cool under nitrogen overnight at room temperature. It is then slowly poured into a vigorously stirred slurry of ice and water (120 g total), and the resulting yellow precipitate filtered, washed with water until neutral to litmus, and transferred to a 500-ml beaker containing 150 ml of aqueous saturated sodium bicarbonate. This mixture is stirred for 10 minutes, then 150 ml of chloroform is added and stirred for an additional 10 minutes. The organic layer is taken up in three 50-ml portions of chloroform, and the solutions are combined and washed once with 150 ml of water. The chloroform solution is dried over anhydrous magnesium sulfate, filtered and evaporated on a rotary evaporator to give a viscous yellow oil. The product is pumped under vacuum overnight to give a yellow solid that is purified by column chromatography on silica gel using 70 percent toluene/30 percent ethyl acetate as the eluent. The infrared, $^1$H and $^{13}$C. nuclear magnetic resonance, and carbon, hydrogen, nitrogen analyses are run.

| Analysis | Calculated | Found |
|---|---|---|
| carbon | 69.60 | 69.30 |
| hydrogen | 3.60 | 3.70 |
| nitrogen | 12.50 | 12.34 |

The yield is 5.7 g equal to 56.5 percent. The melting point is 55° C.–60° C.

EXAMPLE 2

In a one-liter, one-necked, flash dispersed with nitrogen is placed 10 g (0.413 mole) of maleamic acid, 8.57 g (0.0840 mole) of acetic anhydride, 0.2314 g (0.0013 mole) of nickel (II) acetate, 429 ml of acetone and 8.6 ml (6.24 g) of triethylamine. This solution is stirred under nitrogen for about 64 hours. Stirring is stopped and the solution is poured into 300 ml of water saturated with sodium carbonate. Chloroform (150 ml) is added to extract the organic layer. The sodium carbonate comes out of solution, collecting in the bottom of the separatory funnel. Extra water is added to the contents in the funnel to redissolve the sodium carbonate. The organic layer is then extracted and two 150-ml chloroform extractions are performed. The three chloroform extractions are combined and washed with 300 ml of water, dried over magnesium sulfate, filtered and rotovaped. A yellowish-brown oil is obtained and dried under vacuum for about 16 hours to remove remaining chloroform. Using a column packed with silica gel and a solvent of 70 percent toluene, 30 percent ethylacetate, the product is chromatographed. The combined samples containing the product (found by TLC) are rotovaped and pumped under vacuum for about 16 hours. Yield is 8.97 g of product.

EXAMPLE 3

Preparation of Poly-N-[5-(1-cyanobenzocyclobutenyl)]maleimide

Into a 25-ml, two-necked flask equipped with a reflux condenser, nitrogen inlet and magnetic stir bar is placed 0.5 g (2.2 mmole) of N-[5-(1-cyanobenzocyclobutenyl)-]maleimide and 15 ml of mesitylene. The mixture is purged with nitrogen and heated with stirring. Initially, all of the maleimide derivative dissolves to give a clear yellow solution. Upon reaching reflux, the solution becomes cloudy and a beige powder precipitates. After 2 hours of reflux, the reaction is cooled and the precipitated polymer is filtered off and washed free of residual mesitylene with chloroform and dried. The yield is quantitative.

EXAMPLE 4

Into a 25-ml, one-necked, round-bottomed flask equipped with a nitrogen inlet is placed 0.1 g (0.446 mmole) of N-[5-(1-cyanobenzocyclobutenyl)]maleimide. The flask is purged with nitrogen and immersed in an oil bath. The bath temperature is raised to 200° C. over 1 hour. After heating at 200° C. for 20 minutes, the melted monomer solidifies to a pale yellow transparent solid. The flask is cooled and the polymer removed by breaking it up with a spatula. The yield is quantitative.

EXAMPLE 5

Preparation of 4-Nitrophenyl-4-Benzocyclobutenyl Ketone

Into a 100 ml roundbottom one neck flask equipped with a magnetic stirring bar, a reflux condenser and a nitrogen inlet is placed benzocyclobutene 10 g(96.15 mmol) and 4-nitrobenzoyl chloride 11.9 g(64.2 mmol). To the flask is added $Fe_2O_3$ (0.65 mmol, 1 mol %). The flask is heated to 150° C. under a nitrogen atmosphere with vigorous stirring overnight. The mixture is cooled to room temperature, mixed with chloroform (120 ml) and transferred to a separatory funnel. The dark brown solution is washed with 10 percent aqueous sodium bicarbonate (50 ml) twice, water (50 ml) and brine (50 ml) each once. The solution is dried over magnesium sulfate overnight and filtered through celite. The volatiles are removed on a rotovap to give a deep red-black viscous liquid. The liquid is contacted with 100 ml of n-hexane and heated to boiling. The hot n-hexane is decanted away from the undissolved brown liquid. The hexane treatment is repeated three more times. The resultant yellow n-hexane layers are combined and slowly cooled to room temperature. An off-white solid (rosettes) precipitates out of solution. The solid is isolated by suction filtraton. The filtrate is concentrated to one half of its volume and allowed to stand. The solid recovered has a weight of 4.8 grams (a 30 percent yield). NMR and IR spectra are taken of the solid and the spectra agree with the structure of 4-nitrophenyl-4-benzocyclobutenyl ketone.

EXAMPLE 6

Prepareation of 4-Aminophenyl-4-Benzocyclobutenyl Ketone

Into a 250 ml three neck round bottom flask equipped with a magnetic stirring bar, a reflux condenser with a nitrogen inlet and a thermometer and an equilibrating addition funnel is charged 1.0 g (3.95 mmol) of 4-nitrophenyl-4-benzocyclobutenyl ketone, 4.46 g (19.75 mmol) of ($SnCl_2.2H_2O$) and 100 ml of ethanol. Under a nitrogen atmosphere, the mixture is heated to 60° C. To the mixture, in a slow dropwise manner is added sodium borohydride, 75 mg (1.975 mmol) in 20 ml of ethanol, over a period of 20 minutes. After the addition, the temperature of the mixture is maintained at 60° C. for 30 minutes. The mixture is cooled to 10° C. and 80 ml of water previously chilled is added. Concentrated sodium hydroxide is added until the pH is 7 (4M, NaOH, about 6 ml). The mixture is transferred to a 500 ml round-bottom flask and the ethanol is removed on a rotovap. Thereafter, 100 ml of water is added to the off-while slurry and the aqueous phase is extracted with diethyl ether four times with 100 ml aliquots. The ether extracts are dried over sodium sulfate overnight. The sodium sulfate is filtered from the diethyl ether extracts and the diethyl ether is removed on a rotovap. A bright orange solid (0.87 g) is obtained. The solid is recrystallized using carbon tetrachloride (200 ml) and decolorizing charcoal. The first crop of crystals is a pale yellow solid 0.54 g (61.3%). The carbon tetrachloride is concentrated to 50 ml and left standing overnight. NMR and IR indicate the product is 4-aminophenyl-4-benzocyclobutenyl ketone.

EXAMPLE 7

The Preparation of

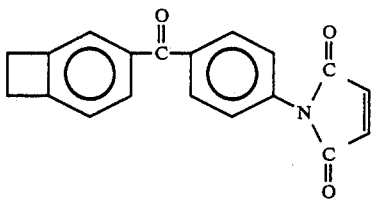

Into a 100 ml round bottom flask equipped with a magnetic stirring bar and a nitrogen inlet is placed 1.0 g(4.482 mmol) of 4-aminophenyl-4-benzocyclobutenyl ketone and 20 ml of acetone. To the solution is added 4.40 g(4.482 mmol) of maleic anhydride in several portions over two minutes, with stirring. The solution is stirred at room temperature for two days. A white solid precipitates. The white solid is believed to be

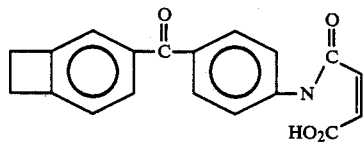

The white solid and the solution described above are stirred with 4.9 mg(8.955 mmol, 0.85 ml) of acetic anhydride, 35 mg(0.142 mmol) of hydrated sodium acetate (four waters of hydration) and 19 drops of triethyl amine. As the triethyl amine is added, the solution turns yellow. Stirring at room temperature is continued overnight. The reaction mixture is an orange hazy mixture (fine solid is present). The reaction mixture is poured into 80 ml of vigorously stirred aqueous sodium bicarbonate. An orange solid precipitates from the solution. To the solution is added 100 ml of chloroform, and the solution is transferred to a separatory funnel. The layers are separated and the aqueous phase is extracted with 100 ml of chloroform. The chloroform extracts are combined and washed with 50 ml of water, and then 50 ml of brine. The solution is dried over magnesium sulfate and the suction filtered through celite. The solvent is removed by a vacuum to give 1.20 g of an orange viscous syrup. The product is recrystallized using ethanol and decolorizing charcoal. The mixture is gravity filtered to give a pale yellow solution. The solution is concentrated to one-half its volume and placed in ice. A white solid precipitates. The solution is allowed to stand overnight. The solid is isolated and dried in air for 1 hour. The weight of the product is, and has a 0.49 g melting point of 138°–139° C. Another 0.39 g of product is further isolated to give a total yield of 0.88 g. The product is exampled by IR and NMR and shows agreement with the following structure,

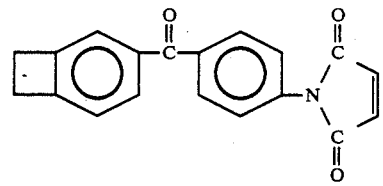

The DSC of the product indicates a melting point of 147° C. and an exotherm is observed at 260.4° C. The energy of the exotherm is 347 J/g. A rescan of the DSC shows no melting point or exotherm but does exhibit a $T_2$ at 260.4° C.

EXAMPLE 8

Polymerization of 4-(N-maleimido)phenyl-4-Benzocyclobutenyl Ketone

Into a tube is placed 146 mg of 4-(N-maleimido)-phenyl-4-benzocyclobutenyl ketone and nitrogen. The tube is palced into a Wood's Metal bath at 150° C. The temperature is controlled and monitored with a heater and a thermocouple. The following sequence of times and temperatures are applied to the tube:

150° C.: 30 min.
180° C.: 30 min.
210° C.: 30 min.
235° C.: 1 hour
260° C.: 1 hour
270° C.: 1 hour At the end of the sequence, the heating is stopped and the tube and the thermocouple are removed from the heating bath. The tube is allowed to cool overnight. The polymer is an amber color with small voids trapped in the matrix. The polymer is physically broken into small pieces. A TGA is run on one of the pieces, 0.05 wt % loss occurs at 327.78° C. and 5% weight loss at 464.39° C.

What is claimed is:

1. A compound which corresponds to the formula

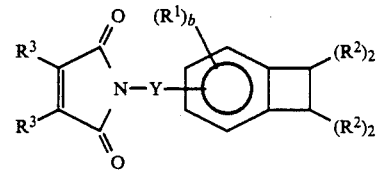

wherein
$R^1$ is separately in each occurrence a hydrocarbyl, hydrocarbylthio, hydrocarbyloxy, electron-withdrawing or electron-donating group;
$R^2$ is separately in each occurrence hydrogen, cyano, halo or an electron donating group;
$R^3$ is separately in each occurrence hydrogen, hydrocarbyl, hydrocarbyloxy or hydrocarbylthio;
Y is a direct bond or a divalent organic radical; and
b is an integer of from 0 to 3, inclusive; with the proviso that at least two of $R^2$ are hydrogen and the further proviso that the moieties $R^1$, $R^2$ and $R^3$ do not interfere with polymerization of the compound.

2. The compound of claim 1 wherein
$R^1$ is $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ arkaryl, $C_{7-20}$ alkaryloxy, $C_{7-20}$ alkarylthio, $C_{7-20}$ aralkyl, $C_{7-20}$ aralkoxy, $C_{7-20}$ aralkylthio, cyano, carboxylate, hydrocarbylcarbonyloxy, nitro, halo, hydrocarbylsulfinyl, hydrocarbylsulfonyl or amino;
$R^2$ is hydrogen, cyano, halo, alkyl or alkoxy;
$R^3$ is hydrogen, $C_{1-20}$ alkyl, $C_{1-20}$ alkoxy, $C_{1-20}$ alkylthio, $C_{6-20}$ aryl, $C_{6-20}$ aryloxy, $C_{6-20}$ arylthio, $C_{7-20}$ alkaryl, $C_{7-20}$ alkaryloxy, $C_{7-20}$ alkarylthio, $C_{7-20}$ aralkyl, $C_{7-20}$ aralkoxy or $C_{7-20}$ aralkylthio; and
b is an integer of 0, 1, 2 or 3.

3. The compound of claim 2 wherein $R^1$ is $C_{1-20}$ alkyl, halo, nitro or cyano; $R^2$ is hydrogen, halo or cyano; and $R^3$ is hydrogen or $C_{1-20}$ alkyl.

4. The compound of claim 3 wherein $R^1$ is $C_{1-3}$ alkyl, halo, nitro or cyano; $R^2$ is hydrogen or cyano; and $R^3$ is hydrogen or $C_{1-3}$ alkyl.

5. The compound of claim 4 wherein $R^2$ is hydrogen; $R^3$ is hydrogen; and b is 0.

6. The compound of claim 5 wherein Y is a direct bond, a hydrocarbylene, hydrocarbyleneamido, hydrocarbylenecarbonyloxy, hydrocarbyleneoxy, hydrocarbyleneamino, hydrocarbylenethio, hydrocarbylenesulfinyl or hydrocarbylenesulfonyl.

7. The compound of claim 6 wherein Y is a direct bond, alkylene, arylene, alkylene-bridged polyarylene, cycloalkylene-bridged polyarylene, alkyleneamido, aryleneamido, alkylenecarbonyloxy, arylenecarbonyloxy, aryleneoxy, alkyleneoxy, aryleneamino, alkyleneamino, alkylenethio, arylenethio, arylenesulfinyl, alkylenesulfinyl, arylenesulfonyl or alkylenesulfonyl.

8. The compound of claim 7 wherein Y is alkylene or arylene.

9. A compound which corresponds to the formula wherein
Ar is a carbocyclic aromatic radical;
$R^1$ is separately in each occurrence a hydrocarbyl, hydrocarbyloxy, hydrocarbylthio, an electron-donating or electron-withdrawing group;
$R^2$ is separately in each occurrence hydrogen, cyano, halo, or electron-donating group;

$R^3$ is separately in each occurrence hydrogen, a hydrocarbyl, hydrocarbyloxy or hydrocarbylthio group;
Y is a direct bond or a divalent organic radical; and
a is an integer of from 0 to 3;
with the proviso that the two carbon atoms of the $(C(R^2)_2)_2$ moiety which are bound to Ar are bound to adjacent carbon atoms on the same aromatic ring of Ar; with the further proviso that at least two of $R^2$ are hydrogen; and the further proviso that the moieties $R^1$, $R^2$ and $R^3$ do not interfere with polymerization of the compound.

10. A monomer which corresponds to the formula wherein
$R^1$ is separately in each occurrence an electron-withdrawing or electron-donating group;
$R^2$ is separately in each occurrence hydrogen, a cyano, an alkoxy, a halo, or an alkyl group;
$R^3$ is separately in each occurence hydrogen, hydrocarbyl, hydrocarbyloxy or hydrocarbylthio;
Y is a direct bond; and
b is an integer of from 0 to 3, inclusive with the proviso that at least two of $R^2$ are hydrogen with the further proviso that $R^1$, $R^2$ and $R^3$ do not interfere with polymerization of the monomer.

11. The compound of claim 10 wherein $R^2$ is separately in each occurrence hydrogen or cyano.

12. The compound of claim 10 which corresponds to the formula

13. The compound of claim 10 which correponds to the formula

* * * * *

UNITED STATES PATENT AND TRADEMARK OFFICE
CERTIFICATE OF CORRECTION

PATENT NO. : 4,826,997

DATED : May 2, 1989

INVENTOR(S) : Robert A. Kirchoff

It is certified that error appears in the above-identified patent and that said Letters Patent is hereby corrected as shown below:

Col. 1, line 28, "polybenzoxazoles" has been misspelled;

Col. 2, line 3 delete "are";

Col. 2, line 6, delete "polymerizable" and insert -- polymerized --;

Col. 2, line 58, delete "alkaryl" and insert -- aralkyl --;

Col. 3, line 10, "pyridine" has been misspelled;

Col. 4, lines 10-11, delete "bridged polyarylene; and more preferably a direct bond or a";

Col. 4, line 57, "electron - with drawing" has been misspelled;

Col. 5, line 21, delete "aralkoxy" and insert -- alkaryl --;

UNITED STATES PATENT AND TRADEMARK OFFICE
CERTIFICATE OF CORRECTION

PATENT NO. : 4,826,997

DATED : May 2, 1989

INVENTOR(S) : Robert A. Kirchoff

It is certified that error appears in the above-identified patent and that said Letters Patent is hereby corrected as shown below:

Col. 5, lines 43-44, "hydrocarbyleneamino" has been misspelled;

Col. 6, line 23, "groups" has been misspelled;

Col. 6, line 44, "Hydrocarbylenecarbonyloxy" has been misspelled;

Col. 7, line 38, after "clobutenylamidohexyl maleimide," insert -- N-benzocyclobutenylamidophenyl maleimide --;

Col. 9, line 18, "chlorobenzenes" has been misspelled;

Col. 12, line 61, "with" has been misspelled;

Col. 13, line 6, "N-arylcyclobutenylamido" has been misspelled;

Col. 13, line 35, "contacted" has been misspelled;

UNITED STATES PATENT AND TRADEMARK OFFICE
CERTIFICATE OF CORRECTION

PATENT NO. : 4,826,997

DATED : May 2, 1989

INVENTOR(S) : Robert A. Kirchoff

It is certified that error appears in the above-identified patent and that said Letters Patent is hereby corrected as shown below:

Col. 18, line 20 "sulfonate" has been misspelled;

Col. 21, line 38, before "alkanol" delete "the" and insert -- an --;

Col. 22, line 49, after "with" delete "a";

Col. 25, line 57, "polymeric" has been misspelled;

Col. 29, line 50, delete "flash" and insert -- flask --;

Col. 29, line 67, "5-nitro-1-cyanobenzocyclobutene" has been misspelled;

Col. 30, line 6, "dispersion" has been misspelled;

Col. 30, line 38, delete "flash" and insert -- flask --;

UNITED STATES PATENT AND TRADEMARK OFFICE
CERTIFICATE OF CORRECTION

PATENT NO. : 4,826,997  Page 4 of 5
DATED : May 2, 1989
INVENTOR(S) : Robert A. Kirchoff It is certified that error appears in the above-identified patent and that said Letters Patent is hereby corrected as shown below:

Col. 30, line 66 delete "flash" and insert -- flask --;

Col. 31, line 37, delete "flash" and insert -- flask --;

Col. 32, line 54, "Preparation" has been misspelled;

Col. 33, line 5, delete "off-while" and insert -- off-white --;

UNITED STATES PATENT AND TRADEMARK OFFICE
CERTIFICATE OF CORRECTION

PATENT NO. : 4,826,997
DATED : May 2, 1989
INVENTOR(S) : Robert A. Kirchoff

It is certified that error appears in the above-identified patent and that said Letters Patent is hereby corrected as shown below:

Col. 34, line 5, delete "exampled" and insert -- examined --;

Col. 34, line 28, "placed" has been misspelled;

Col. 35, line 6, delete "arkaryl" and insert -- alkaryl --.

Signed and Sealed this

Twenty-ninth Day of September, 1992

Attest:

DOUGLAS B. COMER

*Attesting Officer*  *Acting Commissioner of Patents and Trademarks*